United States Patent [19]
Fujii et al.

[11] Patent Number: 5,049,604
[45] Date of Patent: Sep. 17, 1991

[54] PROCESS FOR PRODUCING PIPERIDINE DERIVATIVE AND STABILIZED RESIN COMPOSITION CONTAINING SAID DERIVATIVE

[75] Inventors: Takeo Fujii, Toyonaka; Tamaki Ishii, Suita; Shinichi Yachigo, Toyonaka; Tatsuo Kaneoya, Toyonaka; Yukoh Takahashi, Toyonaka; Yuzo Maegawa, Ibaraki; Haruki Okamura, Osaka; Eizo Okino, Nishinomiya, all of Japan

[73] Assignee: Sumitomo Chemical Company, Limited, Osaka, Japan

[21] Appl. No.: 600,160

[22] Filed: Oct. 19, 1990

Related U.S. Application Data

[63] Continuation of Ser. No. 436,699, Nov. 15, 1989, abandoned, which is a continuation of Ser. No. 754,582, Jul. 15, 1985, abandoned.

[30] Foreign Application Priority Data

Jul. 24, 1984 [JP] Japan ................... 59-154633
Jul. 30, 1984 [JP] Japan ................... 59-161346

[51] Int. Cl.$^5$ ........................................... C08K 5/3435
[52] U.S. Cl. ................................... 524/103; 524/153; 524/291
[58] Field of Search ........................................ 524/103

[56] References Cited

U.S. PATENT DOCUMENTS 4,348,524 9/1982 Karrer et al. ................... 546/187
4,500,662 2/1985 Lai .................................. 546/190

FOREIGN PATENT DOCUMENTS 0062322 10/1982 European Pat. Off. .
3233353 4/1983 Fed. Rep. of Germany .
2107719 5/1983 United Kingdom .
2136805 9/1984 United Kingdom .

Primary Examiner—Veronica P. Hoke
Attorney, Agent, or Firm—Stevens, Davis, Miller & Mosher

[57] ABSTRACT

A stabilized resin composition comprising a resin, a piperidine derivative represented by the formula (III)

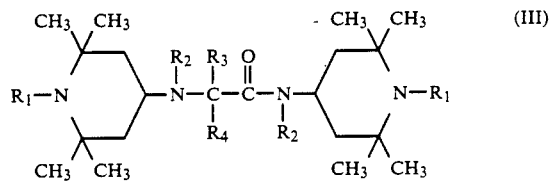

wherein $R_1$ is a hydrogen atom or an alkyl group having 1 to 3 carbom atoms; $R_2$ is a hydrogen atom or an alkyl group having from 1 to 2 carbon atoms; and $R_3$ and $R_4$ are each independently an alkyl group having 1 to 12 carbon atoms, a phenol-type antioxidant and a sulfur-containing antioxidant. The composition simultaneously meets heat resistance, oxidation resistance and light resistance requirements.

7 Claims, No Drawings

PROCESS FOR PRODUCING PIPERIDINE DERIVATIVE AND STABILIZED RESIN COMPOSITION CONTAINING SAID DERIVATIVE

This application is a continuation of application Ser. No. 436,699, filed Nov. 15, 1989, now abandoned, which in turn is a continuation of application Ser. No. 754,582, filed July 15, 1985, now abandoned.

BACKGROUND OF THE INVENTION

1. Field of the Invention

This invention relates to a process for producing a piperidine derivative and to a stabilized resin composition containing said derivative. More particularly, this invention relates to a process for producing a piperidine derivative represented by the general formula (III)

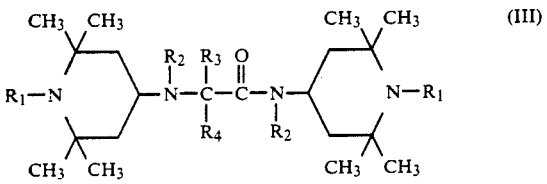

wherein $R_1$ is a hydrogen atom or an alkyl group having 1 to 3 carbon atoms; $R_2$ is a hydrogen atom or an alkyl group having 1 to 12 carbon atoms; and $R_3$ and $R_4$ is each independently an alkyl group having 1 to 12 carbon atoms,
and to a resin composition containing said piperidine derivative which has extremely excellent stability not only to heat and oxidation but also to light.

2. Description of the Prior Art

The piperidine derivative represented by the above-mentioned general formula (III) which is an object of this invention, is known to be useful as a light stabilizer for high molecular substances such as plastics, rubbers and fibers.

There has already been known as a process for producing the piperidine derivative represented by the general formula (III) a process which comprises reacting 4-amino-2,2,6,6-tetramethylpiperidine (in the general formula (I) which will be shown later, $R_1$ and $R_2$ are each H) with α-bromo-α,α-dimethyl-N-2,2,6,6-tetramethyl-4-piperidinylacetamide (Japanese Patent Application Kokai (Laid-Open) No. 176939/82).

However, the above known process requires an extremely special raw material, such as α-bromo-α,α-dimethyl-N-2,2,6,6-tetramethyl-4-piperidinylacetamide, and further gives a low yield of intended product as low as 69%, so that it can hardly be deemed as an industrially satisfactory process for production.

Under these circumstances, the present inventors have made intensive studies to find an industrially advantageous process for producing the piperidine derivative represented by the general formula (III). As a result, it has been found that the intended product can be obtained selectively and without requiring the special raw material, α-bromo-α,α-dialkyl-N-2,2,6,6-tetramethyl-4-piperidinylacetamide, by reacting a piperidine represented by the general formula (I) shown later and a ketone in the presence of chloroform, alkali and in the presence or absence of a phase transfer catalyst, and thus the present invention has been accomplished.

In the meantime, it is well known that such resins as polyethylene, polypropylene, polyvinyl chloride, polyurethane and ABS resin deteriorate by the action of heat, light and oxygen and undergo marked decrease of mechanical properties accompanied by such phenomena as softening, brittleness, surface crazing and discoloration.

It has been already known for the purpose of preventing such deterioration caused by heat and oxidation to use various kinds of phenol-type compounds such as 2,6-di-t-butyl-4-methylphenol and tris(3,5-di-t-butyl-4-hydroxybenzyl) isocyanurate; for the purpose of further improving the oxidation preventing property to use sulfur-containing compounds such as dilauryl thiodipropionate and pentaerythritol tetrakis(3-dodecylthiopropionate) in combination with said phenol-type antioxidant; and further for the purpose of preventing deterioration by light to use jointly light stabilizers including, for example, benzophenone compounds such as 2-hydroxy-4-n-octoxy-benzophenone, benzotriazole compounds such as 2-(2-hydroxy-3-t-butyl-5-methylphenyl)-5-chloro-benzotriazole and 2-(2-hydroxy-3,5-dipentylphenyl)benzotriazole, cyanoacrylate compounds such as 2-cyano-3,3-diphenylacrylate, Ni-containing compounds such as Ni salt of bis(3,5-di-t-butyl-4hydroxybenzylphosphoric acid) monoethyl ester, and hindered piperidine compounds such as 4-benzoyloxy2,2,6,6-tetramethylpiperidine, bis(2,2,6,6-tetramethyl4-piperidyl) sebacate, and a reaction product of N,N'-bis(2,2,6,6-tetramethyl-4-piperidyl)hexylenediamine with 2,4-dichloro-6-t-octylamino-1,3,5-triazine.

However, even in stabilized resin compositions obtained by using these known stabilizers in combination, the requirements for heat resistance, oxidation resistance and light resistance are not met simultaneously.

For example, when a phenol-type compound and a sulfur-containing compound are used as antioxidants, and a benzophenone compound, benzotriazole compound, cyanoacrylate compound, Ni-containing compounds, or the like is used jointly as a light stabilizer, the resulting products are not fully satisfactory in their light resistance. Further, in cases where hindered piperidine compounds commonly used as a light stabilizer are employed, when a sulfur-containing stabilizer is used in combination therewith, there occurs, presumably owing to antagonism, a serious problem that the excellent light-stabilizing effect inherent to the hindered piperidine compounds is lowered extremely. Consequently, selection have to be made between either to use jointly phenol-type stabilizers alone without using sulfur-containing stabilizer to enhance the light resistance at the sacrifice of the resistance to heat and oxidation or alternatively to use also sulfur-containing stabilizers together to enhance the resistance to heat and oxidation at the sacrifice of the light resistance. Thus, even stabilizer systems using a hindered piperidine compound in combination cannot give fully satisfactory resistances to heat, oxidation and light simultaneously.

The present inventors have made intensive studies to solve these problems and resultantly found that the requirements for heat resistance, oxidation resistance and light resistance can be satisfied simultaneously by using a specified piperidine derivative in combination with a sulfur-containing antioxidant and a phenol-type antioxidant without extreme lowering of light resistance as experienced in combinations of various conventional hindered piperidine compounds with sulfur-containing antioxidants, and thus accomplished this invention.

SUMMARY OF THE INVENTION

An object of this invention is to provide a process for producing a piperidine derivative represented by the above-mentioned general formula (III) in an industrially very advantageous way and at a low cost.

Another object of this invention is to provide a stabilized resin composition containing said piperidine derivative.

According to this invention, there is provided an industrially extremely excellent process for producing a piperidine derivative represented by the general formula (III)

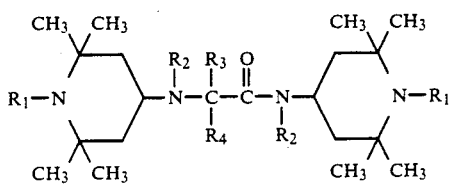

wherein $R_1$ is a hydrogen atom or an alkyl group having 1 to 3 carbon atoms; $R_2$ is a hydrogen atom or an alkyl group having 1 to 12 carbon atoms; and $R_3$ and $R_4$ are each independently an alkyl group having 1 to 12 carbon atoms,
which process comprises reacting a piperidine represented by the general formula (I)

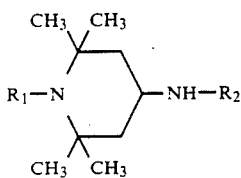

wherein $R_1$ and $R_2$ are as defined above,
with a ketone represented by the general formula (II)

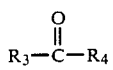

wherein $R_3$ and $R_4$ are as defined above,
in the presence of chloroform and alkali and in the presence or absence of a phase transfer catalyst.

Further, according to this invention, there is provided an extremely excellent stabilized resin composition comprising a resin, a piperidine derivative represented by the general formula (III)

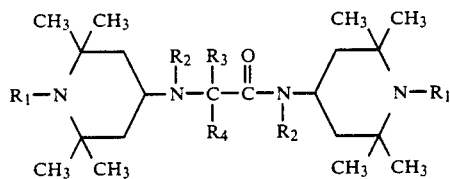

wherein $R_1$, $R_2$, $R_3$ and $R_4$ are as defined above, a phenol-type antioxidant and a sulfur-containing antioxidant which composition can satisfy the requirements not only for resistance to heat and oxidation but also simultaneously resistance to light.

Specific examples of piperidines represented by the general formula (I) in this invention include 4-amino-2,2,6,6-tetramethylpiperidine, 4-amino-1,2,2,6,6-pentamethylpiperidine, 4-amino-1-ethyl-2,2,6,6-tetramethylpiperidine, 4-N-butylamino-2,2,6,6-tetramethylpiperidine, 4-N-butylamino-1,2,2,6,6-pentamethylpiperidine, 4-N-octylamino-2,2,6,6-tetramethylpiperidine, 4-N-octylamino-1,2,2,6,6-pentamethylpiperdine, 4-N-laurylamino-2,2,6,6-tetramethylpiperidine, and 4-N-laurylamino-1,2,2,6,6-pentamethylpiperidine.

The reaction of the piperidines represented by the general formula (I) with the ketones represented by the general formula (II) in the presence of a phase transfer catalyst is conducted under the following conditions.

Examples of ketones represented by the general formula (II) include acetone, methyl ethyl ketone, methyl isopropyl ketone, methyl isobutyl ketone, and 2-nonanone. These ketones are used in an amount of generally 0.5 to 2 moles, preferably 0.5 to 1 mole, relative to 1 mole of the piperidines represented by the general formula (I).

The amount of chloroform used in this invention is usually 0.5 to 4 moles, preferably 0.5 to 2 moles, relative to 1 mole of the piperidines represented by the general formula (I).

Alkalis usable in this invention include hydroxide of alkali metals and alkaline earth metals. For example, sodium hydroxide, potassium hydroxide, calcium hydroxide and the like are usually used. The amount of the alkalis to be used is usually 1 to 4 moles, preferably 1.5 to 3 moles, relative to 1 mole of the piperidines represented by the general formula (I). They can be used either as an aqueous solution or directly as a solid.

There is no specific restriction as to the phase transfer catalysts, which include, for example, benzyltrimethylammonium chloride, benzyltriethylammonium chloride, tetrabutylammonium bromide, tetrabutylphosphonium chloride, trioctylmethylammonium chloride, and tetraphenylphosphonium bromide. The amount of said catalyst to be used is generally 0.0001 to 0.01 mole, preferably 0.001 to 0.005 mole, relative to 1 mole of the piperidines represented by the general formula (I).

The reaction of the piperidines represented by the general formula (I) with the ketones represented by the general formula (II) in the absence of a phase transfer catalyst is conducted under the following conditions.

Examples of ketones represented by the general formula (II) include acetone, methyl ethyl ketone, methyl isopropyl ketone, methyl isobutyl ketone, and 2-nonanone. These ketones are used in an amount of generally 0.5 to 30 moles, preferably 0.5 to 20 moles, relative to 1 mole of the piperidines represented by the general formula (I).

The amount of chloroform used in this invention is usually 0.5 to 2 moles, preferably 0.5 to 1 mole, relative to 1 mole of the piperidines represented by the general formula (I).

Alkalis usable in this invention include hydroxide of alkali metals and alkaline earth metals. For example, sodium hydroxide, potassium hydroxide, calcium hydroxide and the like are usually used. The amount of the alkalis to be used is usually 1 to 4 moles, preferably 1.5 to 3 moles, relative to 1 mole of the piperidines represented by the general formula (I). They can be used either as an aqueous solution or directly as a solid.

The reaction is usually conducted in the presence of excess chloroform or starting ketones at a temperature of −30° to 60° C., preferably −10° to 30° C. However, other solvents may be used as occasion demands. In such cases, examples of the other solvents include aliphatic hydrocarbons such as hexane and heptane; aromatic hydrocarbons such as benzene, toluene and xylene; water soluble polar solvents such as N,N-dimethylformamide, dimethyl sulfoxide, dioxane, and sulfolane; alcohols such as methanol, ethanol, propanol, isopropyl alcohol, butanol, t-butanol, n-amyl alcohol, isoamyl alcohol, 2-ethylhexyl alcohol and cyclohexanol; and glycol ethers such as ethylene glycol monomethyl ether, ethylene glycol monoethyl ether and ethylene glycol monobutyl ether. These are used each alone or in a combination of two or more thereof.

Typical piperidine derivatives of this invention produced as mentioned above are shown in Table 1.

TABLE 1

| Compound No. | $R_1$ | $R_2$ | $R_3$ | $R_4$ |
|---|---|---|---|---|
| III-1 | H | H | $CH_3$ | $CH_3$ |
| III-2 | H | H | $CH_3$ | $CH_2CH_3$ |
| III-3 | H | H | $CH_3$ | $CH_2CH(CH_3)_2$ |
| III-4 | $CH_3$ | H | $CH_3$ | $CH_3$ |
| III-5 | H | $(CH_2)_3CH_3$ | $CH_3$ | $CH_3$ |
| III-6 | $CH_3$ | $(CH_2)_3CH_3$ | $CH_3$ | $CH_3$ |
| III-7 | H | H | $CH_3$ | $(CH_2)_6CH_3$ |

In obtaining the stabilized resin composition which is one of the objects of this invention, from the viewpoint of obtaining more excellent light stability, the substituent $R_1$ in the above-mentioned general formula (III) is preferably a hydrogen atom or a methyl group, more preferably a hydrogen atom; $R_2$ is preferably a hydrogen atom or an alkyl group having 1 to 4 carbon atoms, more preferably a hydrogen atom; $R_3$ and $R_4$ are, each independently, preferably of 1 to 7 carbon atoms, more preferably a methyl group.

Examples of phenol-type antioxidants used for obtaining the stabilized resin composition of this invention are selected from the group consisting of 2,6-di-t-butyl-4-methylphenol, n-octadecyl 3-(3,5-di-t-butyl-4-hydroxyphenyl)propionate, 2,2'-methylenebis(4-methyl-6-t-butylphenol), 4,4'-butylidenebis(3-methyl-6-t-butylphenol), 4,4'-thiobis(3-methyl-6-t-butylphenol), 2-t-butyl-6-(3-t-butyl-5-methyl-2-hydroxybenzyl)-4-methylphenyl acrylate, 1,1,3-tris(2-methyl-4-hydroxy-5-t-butylphenyl)butane, 1,3,5-trimethyl-2,4,6-tris(3-alkyl 5-t-butyl-4-hydroxybenzyl)benzene, 1,3,5-tris (3-alkyl-5-t-butyl-4-hydroxybenzyl) isocyanurate, 1,3,5-tris(3-(3-alkyl-5-t-butyl-4-hydroxyphenyl)propionyloxyethyl) isocyanurate, ethylene glycol bis(3,3-bis(4-hydroxy-3-t-butylphenyl)butanoate, and pentaerythritol tetrakis(3-(3-alkyl-5-t-butyl-4-hydroxyphenyl)propionate).

Examples of sulfur-containing antioxidants used in this invention are selected from the group consisting of dilauryl thiodipropionate, dimyristyl thiodipropionate, distearyl thiodipropionate, pentaerythritol tetrakis(3-dodecylthiopropionate), and 3,9-bis(2-dodecylthioethyl)-2,4,8,10-tetraoxaspiro [5.5] undecane.

The stabilized resin composition of this invention contains a specified piperidine derivative represented by the above-mentioned general formula (III), a phenol-type antioxidant and a sulfur-containing antioxidant.

The total content of these stabilizers is usually 0.01 to 5 parts by weight, preferably 0.05 to 2 parts by weight, based on 100 parts by weight of resin. The weight ratio of respective stabilizers is normally 1–20:1–15 in terms of compound (III):phenol-type antioxidant:sulfur-containing antioxidant.

For compounding the resin composition, conventional apparatuses and operation procedures used for incorporating stabilizers, pigments, fillers and the like into resins can be employed with little or no alteration.

The stabilizers for resin of this invention may be used jointly with other ingredients including, for example, antioxidants, light stabilizers, sequestering agents, metallic soaps, nucleating agents, lubricants, antistatic agents, flame retardants, pigments and fillers.

Particularly, the color of the resin composition can be improved by jointly using phosphite antioxidants as the antioxidants.

Examples o the phosphite antioxidants include tris(-nonylphenyl) phosphite, distearyl pentaerythritol diphosphite, tris(2,4-di-t-butylphenyl) phosphite, tris(2-t-butyl-4-methylphenyl) phosphite, bis(2,4-di-t-butylphenyl) pentaerythritol diphosphite, and tetrakis(2,4-di-t-butylphenyl)-4,4'-biphenylene diphosphonite.

The light stability of the composition of this invention can be further improved by adding light stabilizers other than the above-mentioned piperidine derivatives represented by the general formula (III). These light stabilizers include, for example, benzophenone compounds such as 2-hydroxy-4-methoxybenzophenone, 2-hydroxy-n-octoxybenzophenone and 2,2'-dihydroxy-4,4'-dimethoxybenzophenone; benzotriazole compounds such as 2-(2-hydroxy-3-t-butyl-5-chlorobenzotriazole, 2-(2-hydroxy-3,5-dipentylphenyl)benzotriazole, 2-(2-hydroxy-3-t-butyl-5-methylphenyl)benzotriazole, 2-(2-hydroxy-5-methylphenyl)benzotriazole, 2-(2-hydroxy-3,5-di-t-butylphenyl)benzotriazole, 2-(2-hydroxy-3,5-di-t-butylphenyl)-5-chlorobenzotriazole, 2-(2-hydroxy-5-t-octylphenyl)benzotriazole, and 2-(2-hydroxy-3,5-di-($\alpha,\alpha$-dimethylbenzyl)phenyl)benzotriazole; benzoate-type compounds such as phenyl salicylate, p-t-butylphenyl salicylate, 2,4-di-t-butylphenyl 3',5'-di-t-butyl-4'-hydroxybenzoate, and hexadecyl 3,5-di-t-butyl-4-hydroxybenzoate: Ni compounds such as Ni salt of dibutyldithiocarbamic acid, [2,2'-thiobis(4-toctylphenolate)]-n-butylamine Ni complex and Ni salt of bis(3,5-di-t-butyl-4-hydroxybenzylphosphoric acid) monoethyl ester; cyanoacrylate compounds such as ethyl 2-cyano-3,3-diphenylacrylate; and oxalic acid diamides such as N-2-ethylphenyl-N'-2-ethoxy-5-t-butylphenyl oxalic acid diamide and N-2-ethylphenyl-N'-2-ethoxyphenyl oxalic acid diamide.

Examples of resins which can be stabilized according to this invention include poly-$\alpha$-olefins such as low density polyethylene, medium to high density polyethylene, linear low density polyethylene, polypropylene and polybutene-1; $\alpha$-olefin copolymers such as propylene-ethylene random or block copolymer and ethylene-butene-1 random copolymer; copolymers of poly-$\alpha$-olefin with vinyl monomers such as maleic anhydride-modified polypropylene; or mixtures thereof; chlorinated polyethylene, EVA resin, polyvinyl chloride, methacrylic resin, polystyrene, high impact polystyrene, ABS resin, AES resin, MBS resin, polyethylene terephthalate, polybutylene terephthalate, polyamide, polyimide, polycarbonate, polyacetal, polyurethane, and unsaturated polyester resin. Further, these resins may be blended with rubbers such as isoprene rubber, butadiene rubber, acrylonitrile-butadiene copolymer rubber, styrene-butadiene copolymer rubber and ethylene-propylene rubber.

This invention will be described in more detail below with reference to Examples, but it is not limited thereto.

EXAMPLE 1

Preparation of compound No. III-1

Into a four-necked flask equipped with a thermometer and a stirrer, were placed 156 g of 4-amino-2,2,6,6-tetramethylpiperidine, 32 g of acetone, 239 g of chloroform and 0.4 g of benzyltrimethylammonium chloride, and the mixture was cooled down to 5° C. with stirring. Then, 257.6 g of 50% aqueous potassium hydroxide solution was added dropwise thereto over a period of 1 hour while the inner temperature was maintained at 5° to 10° C., and the resulting mixture was allowed to react at a temperature of 5° to 10° C. for 5 hours.

After completion of the reaction, the reaction liquid was separated into two layers, the aqueous layer was discarded, and excess chloroform in the organic layer was distilled off to obtain 176 g of white crystals. Yield: 92.6%; m.p.: 127°–128° C. Parent ion peak of 380 was confirmed by FD-mass analysis.

EXAMPLE 2

Preparation of compound No. III-2

Reaction and after-treatment were carried out in the same manner as in Example 1 except that 39.6 g of methyl ethyl ketone was used in place of acetone used in the Example to obtain 177 g of white crystals. Yield: 89.8%; m.p.: 108°–109° C. Parent ion peak of 394 was confirmed by FD-mass analysis.

EXAMPLE 3

Preparation of compound No. III-3

Reaction was carried out in the same manner as in Example 1 except that 55 g of methyl isobutyl ketone was used in place of acetone used in the Example. After removing excess chloroform by distillation and recrystalized from n-hexane, 175 g of white crystals were obtained. Yield: 80.8%; m.p.: 109°–110° C. Parent ion peak of 422 was confirmed by FD-mass analysis.

EXAMPLE 4

Preparation of compound No. III-4

Reaction and after-treatment were carried out in the same manner as in Example 1 except that 170 g of 4-amino-1,2,2,6,6-pentamethylpiperidine was used in place of the piperidine compound used in the Example to obtain 184 g of a viscous liquid in 90.2% yield. Parent ion peak of 408 was confirmed by FD-mass analysis.

EXAMPLE 5

Preparation of compound No. III-7

Reaction and after-treatment were carried out in the same manner as in Example 3 except that 78 g of 2-nonanone was used in place of methyl isobutyl ketone used in the Example to obtain 168 g of white crystals. Yield: 72.4%; m.p.: 100°–101° C. Parent ion peak of 464 was confirmed by FD-mass analysis.

EXAMPLE 6

Preparation of compound No. III-1

Into a four-necked flask equipped with a thermometer and a stirrer, were placed 100 g of 4-amino-2,2,6,6-tetramethylpiperidine, 600 g of acetone and 54.5 g of chloroform, and the mixture was cooled down to 5° C. with stirring. Then, 64 g of a solid potassium hydroxide was added little by little over a period of one hour, while the inner temperature was maintained at 5° to 10° C., and the resulting mixture was allowed to react at a temperature of 0° to 10° C. for 4 hours.

After completion of the reaction, potassium chloride formed was separated by filtration, and 500 g of acetone was distilled off from the filtrate (acetone solution). White crystals isolated from the concentrated acetone solution were filtered and dried to obtain 110 g of the product. Yield: 91%; m.p.: 127°–128° C. Parent ion peak of 380 was confirmed by FD-mass analysis.

EXAMPLE 7

Preparation of compound No. III-2

Reaction and after-treatment were carried out in the same manner as in Example 6 except that methyl ethyl ketone was used in place of acetone to obtain 108 g of white crystals. Yield: 85.3%; m.p.: 108°–109° C. Parent ion peak of 394 was confirmed by FD-mass analysis.

EXAMPLE 8

Preparation of compound No. III-3

Reaction and after-treatment were carried out in the same manner as in Example 6 except that methyl isobutyl ketone was used in place of acetone and the resulting product was recrystalized from n-hexane to obtain 107 g of white crystals. Yield: 76.3%; m.p.: 109°–110° C. Parent ion peak of 422 was confirmed by FD-mass analysis.

EXAMPLE 9

Preparation of compound No. III-4

Reaction and after-treatment were carried out in the same manner as in Example 6 except that 109 g of 4-amino-1,2,2,6,6-pentamethylpiperidine was used in place of 100 g of 4-amino-2,2,6,6-tetramethylpiperidine to obtain 118 g of a viscous liquid. Yield: 90.2%. Parent ion peak of 408 was confirmed by FD-mass analysis.

EXAMPLE 10

Preparation of compound No. III-7

Reaction and after-treatment were carried out in the same manner as in Example 8 except that 2-nonane was used in place of methyl isobutyl ketone to obtain 116 g of white crystals. Yield: 78.2%; m.p.: 100°–101° C. Parent ion peak of 464 was confirmed by FD-mass analysis.

EXAMPLE 11

Compounding ingredients shown below were blended in a mixer for 5 minutes and then melt-kneaded in mixing rolls at 180° C. The compound thus obtained was formed into a sheet of 1 mm thickness in a hot press at 210° C., from which test pieces 150×30×1 mm in size were prepared.

The test pieces were irradiated with light in a sunshine weather-O-meter (light source: carbon arc, black panel temperature, 83±3° C., spraying cycle: 120 minutes, spraying time: 18 minutes) and were bent almost double every 60 hours. The time which had elapsed until the specimen broke by bending was determined to evaluate the weather resistance of the specimen.

Meanwhile, test pieces 40×40×1 mm in size were prepared and placed in a Geer oven at 160° C. to determine the period of time which had elapsed until 30% of the one side surface of the test piece became brittle. The time was regarded as the induction period for thermal brittleness and used to evaluate thermal and oxidation stability.

The results obtained are shown in Table 2.

| Compounding composition | |
|---|---|
| Unstabilized polypropylene | 100 parts by wt. |
| Calcium stearate | 0.1 parts by wt. |
| 2,6-Di-t-butyl-4-methylphenol | 0.05 parts by wt. |
| Test compound { Light stabilizer | 0.2 parts by wt. |
| Phenol-type compound | 0.05 parts by wt. |
| Sulfur-containing compound | 0.25 parts by wt. |

In Table 2, UVA-1 to AO-3 refer to the following compounds.

| | |
|---|---|
| UVA-1 | 2-Hydroxy-4-n-octoxybenzophenone |
| UVA-2 | 2-(2-Hydroxy-3-t-butyl-5-methylphenyl)-5-chlorobenzotriazole |
| UVA-3 | 2-(2-Hydroxy-3,5-dipentylphenyl)benzotriazole |
| UVA-4 | Ethyl 2-cyano-3,3-diphenylacrylate |
| UVA-5 | Ni salt of bis(3,5-di-t-butyl-4-hydroxybenzyl-phosphoric acid) monoethyl ester |
| UVA-6 | Bis(2,2,6,6-tetramethyl-4-piperidyl) sebacate |
| UVA-7 | Tinuvin 944 (a trade name, mfd. by Ciba Geigy Corp.) (Hindered piperidine-type light stabilizer) |
| AO-1 | Tris(3,5-di-t-butyl-4-hydroxybenzyl) iso-cyanurate |
| AO-2 | Dilauryl 3,3'-thiodipropionate |
| AO-3 | Pentaerythritol tetrakis(3-dodecylthiopropionate) |

TABLE 2

| No. | Light stabilizer | Phenol compound | Sulfur compound | Light stability (hours) | Induction period for thermal brittleness (hours) |
|---|---|---|---|---|---|
| Example of this invention | | | | | |
| 1 | III-1 | AO-1 | AO-2 | 1980 | 795 |
| 2 | III-2 | " | " | 1920 | 780 |
| 3 | III-3 | " | " | 1860 | 770 |
| 4 | III-4 | " | " | 1920 | 790 |
| 5 | III-5 | " | " | 1800 | 750 |
| 6 | III-6 | " | " | 1800 | 740 |
| 7 | III-1 | " | AO-3 | 1980 | 780 |
| 8 | III-2 | " | " | 1920 | 750 |
| 9 | III-3 | " | " | 1860 | 730 |

TABLE 2-continued

| No. | Light stabilizer | Phenol compound | Sulfur compound | Light stability (hours) | Induction period for thermal brittleness (hours) |
|---|---|---|---|---|---|
| 10 | III-4 | " | " | 1920 | 770 |
| 11 | III-5 | " | " | 1800 | 720 |
| 12 | III-6 | " | " | 1800 | 700 |
| 13 | III-7 | " | " | 1800 | 760 |
| Comparative Example | | | | | |
| 14 | UVA-1 | AO-1 | AO-2 | 480 | 490 |
| 15 | UVA-2 | " | " | 720 | 500 |
| 16 | UVA-3 | " | " | 480 | 490 |
| 17 | UVA-4 | " | " | 240 | 480 |
| 18 | UVA-5 | " | " | 420 | 485 |
| 19 | UVA-6 | " | " | 960 | 485 |
| 20 | UVA-7 | " | " | 900 | 480 |
| 21 | UVA-1 | " | AO-3 | 480 | 480 |
| 22 | UVA-2 | " | " | 680 | 480 |
| 23 | UVA-3 | " | " | 420 | 480 |
| 24 | UVA-4 | " | " | 240 | 470 |
| 25 | UVA-5 | " | " | 420 | 475 |
| 26 | UVA-6 | " | " | 900 | 475 |
| 27 | UVA-7 | " | " | 840 | 470 |
| 28 | UVA-1 | — | — | 420 | 30 |
| 29 | UVA-2 | — | — | 600 | 45 |
| 30 | UVA-3 | — | — | 420 | 30 |
| 31 | UVA-4 | — | — | 240 | 20 |
| 32 | UVA-5 | — | — | 360 | 30 |
| 33 | UVA-6 | — | — | 1800 | 30 |
| 34 | UVA-7 | — | — | 1680 | 30 |
| 35 | III-1 | — | — | 2280 | 60 |
| 36 | III-2 | — | — | 2160 | 55 |
| 37 | III-3 | — | — | 2100 | 55 |
| 38 | III-4 | — | — | 2220 | 60 |
| 39 | III-5 | — | — | 2040 | 55 |
| 40 | III-6 | — | — | 2040 | 55 |
| 41 | III-7 | — | — | 2040 | 55 |
| 42 | — | AO-1 | AO-2 | 120 | 450 |
| 43 | — | — | " | 120 | 430 |
| 44 | — | — | — | 120 | 5 |

EXAMPLE 12

Test compounds indicated in Table 3 were added to a 25% polyurethane dope (consisting of 25 parts by weight of polyurethane resin, 3.75 parts by weight of dimethylformamide and 71.25 parts by weight of tetrahydrofuran) in an amount of 1% by weight based on the polyurethane resin. The resulting mixture was cast on polyester film to 1.2 mm thickness and dried in a drier at 45° C. for 1 hour.

No. 3 dumbbell test pieces were stamped out from the sheet thus obtained. The test pieces were irradiated with light in a fade meter (light source: ultraviolet ray carbon arc, black panel temperature: 63±3° C.) for 60 and 120 hours and then subjected to a tensile test (stretching velocity: 200 mm/min, temperature: 25° C.) to determine percentage of retention of breaking strength.

The results obtained are shown in Table 3.

TABLE 3

| Test compounds | Example of this invention | | | | | | | Comparative Example | | | |
|---|---|---|---|---|---|---|---|---|---|---|---|
| | 1 | 2 | 3 | 4 | 5 | 6 | 7 | 8 | 9 | 10 | 11 |
| III-1 | 0.7 | | | | | | | | | | None |
| III-2 | | 0.7 | | | | | | | | | |
| III-3 | | | 0.7 | | | | | | | | |
| III-4 | | | | 0.7 | | | | | | | |
| III-5 | | | | | 0.7 | | | | | | |
| III-6 | | | | | | 0.7 | | | | | |
| III-7 | | | | | | | 0.7 | | | | |
| UVA-1 | | | | | | | | 0.7 | | | |
| UVA-3 | | | | | | | | | 0.7 | | |

TABLE 3-continued

| Test compounds | Example of this invention No. | | | | | | | Comparative Example | | | |
|---|---|---|---|---|---|---|---|---|---|---|---|
| | 1 | 2 | 3 | 4 | 5 | 6 | 7 | 8 | 9 | 10 | 11 |
| UVA-6 | | | | | | | | | | 0.7 | |
| AO-1 | 0.05 | 0.05 | 0.05 | 0.05 | 0.05 | 0.05 | 0.05 | 0.05 | 0.05 | 0.05 | |
| AO-2 | 0.25 | 0.25 | 0.25 | 0.25 | 0.25 | 0.25 | 0.25 | 0.25 | 0.25 | 0.25 | |
| Retention of breaking strength (%) | | | | | | | | | | | |
| 60 Hours | 85 | 80 | 80 | 85 | 75 | 75 | 75 | 40 | 55 | 55 | 30 |
| 120 Hours | 65 | 60 | 60 | 65 | 55 | 50 | 55 | 20 | 30 | 35 | 15 |

EXAMPLE 13

A compound shown below was extrusion-molded at 200° C. into pellets. The pellets were injection-molded at 230° C. to form test pieces of 2 mm thickness.

The test pieces were irradiated in a fade meter (light source: ultraviolet ray carbon arc, black panel temperature: 63±3° C.) for 1500 hours. The degree of discoloration was evaluated by the color difference $\Delta Y_I$ from that of the specimen before irradiation.

The results obtained are shown in Table 4.

| Compounding composition | |
|---|---|
| ABS resin | 100 parts by wt. |
| Pentaerythritol tetrakis (3-(3,5-di-t-butyl-4-hydroxyphenyl)-propionate) | 0.05 parts by wt. |
| Distearyl 3,3'-thiodipropionate | 0.2 parts by wt. |
| Test compound | 0.2 parts by wt. |

TABLE 4

| No. | Test compound | $\Delta Y_I$ |
|---|---|---|
| Example of this invention | | |
| 1 | III-1 | 11.4 |
| 2 | III-2 | 12.7 |
| 3 | III-3 | 13.0 |
| 4 | III-4 | 12.3 |
| 5 | III-5 | 13.1 |
| 6 | III-6 | 13.4 |
| 7 | III-7 | 13.3 |
| Comparative Example | | |
| 8 | UVA-1 | 31.2 |
| 9 | UVA-3 | 28.5 |
| 10 | UVA-6 | 28.1 |
| 11 | None | 43.5 |

What is claimed is:

1. A stabilized resin composition comprising a resin, a piperidine derivative represented by the formula (III)

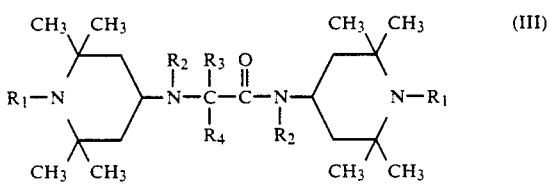

(III)

wherein $R_1$ is a hydrogen atom or an alkyl group having 1 to 3 carbon atoms; $R_2$ is a hydrogen atom or an alkyl group having 1 to 12 carbon atoms; and $R_3$ and $R_4$ are each independently an alkyl group having 1 to 12 carbon atoms, a phenol-type antioxidant and a sulfur-containing antioxidant selected from the group consisting of dilauryl thiodipropionate, dimyristyl thiodipropionate, distearyl thiodipropionate, pentaerythritol tetrakis(3-dodecylthiopropionate) and 3,9-bis(2-dodecylthioethyl)-2,4,8,10-tetraoxaspiro[5.5]-undecane.

2. A stabilized resin composition according to claim 1, wherein in the general formula (III), $R_1$ is a hydrogen atom or a methyl group, $R_2$ is a hydrogen atom or a hydrocarbon group having 1 to 4 carbon atoms, and $R_3$ and $R_4$ are each independently a hydrocarbon group having 1 to 7 carbon atoms.

3. A stabilized resin composition according to claim 1, wherein the phenol-type antioxidant is one member selected from the group consisting of 2,6-di-t-butyl-4-methylphenol, n-octadecyl 3-(3,5-di-t-butyl-4-hydroxyphenyl)propionate, 2,2'-methylenebis(4-methyl-6-t-butylphenol), 4,4'-butylidenebis(3-methyl-6-t-butylphenol), 4,4'-thiobis(3-methyl-6-t-butylphenol), 2-t-butyl-6-(3-t-butyl-5-methyl-2-hydroxybenzyl)-4-methylphenyl acrylate, 1,1,3-tris(2-methyl-4-hydroxy-5-t-butylphenyl)butane, 1,3,5-trimethyl-2,4,6-tris(3-alkyl-5-t-butyl-4-hydroxybenzyl)benzene, 1,3,5-tris(3-alkyl-5-t-butyl-4-hydroxybenzyl) isocyanurate, 1,3,5-tris(3-(3-alkyl-5-t-butyl-4-hydroxyphenyl)propionyloxyethyl) isocyanurate, ethylene glycol bis(3,3-bis(4-hydroxy-3-t-butylphenyl)butanoate, and pentaerythritol tetrakis(3-(3-alkyl-5-t-butyl-4-hydroxyphenyl)propionate).

4. A stabilized resin composition according to claim 1, wherein said resin is poly-α-olefins, α-olefin copolymers, copolymers of poly-α-olefin with a vinyl monomer, chlorinated polyethylene, EVA resin, polyvinyl chloride, methacrylic resin, polystyrene, ABS resin, AES resin, MBS resin, polyethylene terephthalate, polybutylene terephthalate, polyamide, polyimide, polycarbonate, polyacetal, polyurethane, unsaturated polyester resin, or blended products of these resins with isoprene rubber, butadiene rubber, acrylonitrile-butadiene copolymer rubber, styrene-butadiene copolymer rubber or ethylene propylene rubber.

5. A stabilized resin composition according to claim 1, wherein the total amount of the piperidine derivative represented by the general formula (III), the phenol-type antioxidant and the sulfur-containing antioxidant is 0.01 to 5 parts by weight based on 100 parts by weight of the resin and the ratio of said piperidine derivative to the phenol-type antioxidant and the sulfur-containing antioxidant in this order is 1-2:1:1-15 by weight.

6. A stabilized resin composition according to claim 1, wherein a phosphite-type antioxidant is incorporated.

7. A stabilized resin composition according to claim 1, wherein a light stabilizer other than the piperidine derivative represented by the general formula (III) is incorporated.

* * * * *